United States Patent [19]

Braune

[11] Patent Number: 5,561,218
[45] Date of Patent: Oct. 1, 1996

[54] WORKING UP RESIDUES CONTAINING DIHYDROXY COMPOUNDS

[75] Inventor: Peter Braune, Erbes-Büdesheim, Germany

[73] Assignee: BASF Aktiengesellschaft, Ludwigshafen, Germany

[21] Appl. No.: 591,944

[22] Filed: Jan. 23, 1996

Related U.S. Application Data

[63] Continuation-in-part of Ser. No. 314,949, Sep. 29, 1994, abandoned.

[30] Foreign Application Priority Data

Oct. 5, 1993 [DE] Germany .......................... 43 33 929.8

[51] Int. Cl.⁶ ........................................ C08F 6/00
[52] U.S. Cl. ..................... 528/491; 528/272; 528/279; 528/495; 528/501; 528/503; 525/437
[58] Field of Search ...................... 528/272, 279, 528/491, 495, 501, 503; 525/437

[56] References Cited

U.S. PATENT DOCUMENTS

| | | | |
|---|---|---|---|
| 4,056,514 | 11/1977 | Strehler et al. | 528/274 |
| 4,239,882 | 12/1980 | Kimura et al. | 528/295 |
| 4,499,261 | 2/1985 | Heinze et al. | 528/279 |

OTHER PUBLICATIONS

Chemiefasern/Textilindustrie 40 (1992), 1058–1062.
Ullmann's Enzyklopädie der technischen Chemie, 4th Ed. vol. 19, pp. 61–88.

*Primary Examiner*—Samuel A. Acquah
*Attorney, Agent, or Firm*—Keil & Weinkauf

[57] ABSTRACT

A process for working up residues which contain dihydroxy compounds and are obtained in the preparation of polyesters by reacting dicarboxylic acids or their esters or ester-forming derivatives with dihydroxy compounds, a) in a first stage a diester of a dicarboxylic acid with an alkanol being subjected to transesterification with a molar excess of a dihydroxy compound, b) the vapors which are obtained in the reaction according to a) and contain predominantly the alkanol formed in the transesterification, excess dihydroxy compounds and oligomeric and polymeric reaction products being transferred to a column in which the alkanol is separated off via the top and the other products are separated off as a bottom product, and c) the bottom product being then subjected to a further treatment to recover the dihydroxy compound, wherein a liquid residue containing dihydroxy compounds is added in stage b) of the process, and the bottom product is discharged in substantially liquid form from the column and then subjected to a treatment for recovering the dihydroxy compound.

2 Claims, No Drawings

WORKING UP RESIDUES CONTAINING DIHYDROXY COMPOUNDS

This application is a continuation application Ser. No. 08/314,949, filed on Sep. 29, 1994, abandoned.

The present invention relates to a process for working up residues containing dihydroxy compounds, as obtained in the preparation of polyesters by reacting dicarboxylic acids or their esters or ester-forming derivatives with dihydroxy compounds, a) in a first stage a diester of a dicarboxylic acid with an alkanol being subjected to transesterification with a molar excess of a dihydroxy compound, b) the vapors which are obtained in the reaction according to a) and contain predominantly the alkanol formed in the transesterification, excess dihydroxy compounds and oligomeric and polymeric reaction products being transferred to a column in which the alkanol is separated off via the top and the other products are separated off as a bottom product, and c) the bottom product being then subjected to a further treatment to recover the dihydroxy compound.

Polyesters, in particular polyalkylene terephthalates, are prepared in the main by transesterification/polycondensation processes in which a transesterification is carried out in a first stage and the actual polycondensation is effected in at least one further stage (cf. Chemiefasern/Textilindustrie 40 (1992), 1058–1062, and Ullmann's Enzyklopädie der technischen Chemie, 4th Edition, Volume 19, pages 61–88).

This process will be briefly illustrated using as an example the preparation of polybutylene terephthalate from dimethyl terephthalate and 1,4-butanediol.

In a first reaction space, dimethyl terephthalate is subjected to transesterification with a molar excess, preferably 5–60, in particular 10–45, mol %, of 1,4-butanediol, the transesterified compound being subjected to the actual polycondensation in further steps. The vapors obtained in the transesterification are transferred to a column in which a top product consisting of low-boiling methanol and a bottom product which contains small amounts of oligomers, polymers and dimethyl terephthalate in addition to excess 1,4-butanediol are obtained.

Furthermore, the components which are obtained in the actual polycondensation and consist mainly of 1,4-butanediol, oligomers, polymers and dimethyl terephthalate can be passed into this column.

In addition, from 0.05 to 0.1 kg of an esterification or transesterification catalyst, for example tetrabutyl orthotitanate, per 250 kg of bottom product can be used in the bottom of this column to remove the unconverted dimethyl terephthalate.

For economic reasons, it is appropriate to subject this bottom product to a further treatment in order to recover the 1,4-butanediol, which is present in considerable amounts. However, since the bottom product obtained in the known processes has a high viscosity or is a solid (depending on the composition) and therefore is virtually impossible to remove continuously from the column since it cannot be conveyed, problems frequently occur in this methanol column, having an adverse effect on the process. Moreover, the working up of these residues once again gives rise to solids as a bottom product, the incineration of which in turn is complicated and expensive with regard to conveying.

Washing the columns section by section in order to wash out the residues obtained is also disadvantageous for a continuous process.

It is an object of the present invention to improve the working up of the vapors in the methanol columns in the processes described above (which, as is once again pointed out here, can be used in principle for the preparation of polyesters generally and not only for the preparation of polybutylene terephthalate) so that the bottom products obtained can be more readily removed from the column and can be transported for recovery of the dihydroxy compounds.

We have found, surprisingly, that this object is achieved if a liquid residue containing dihydroxy compounds is added in stage b) of a process according to the preamble of the claim, and the bottom product is discharged in substantially liquid form from the column and then subjected to a treatment for recovering the dihydroxy compound.

As a result of the addition of this residue containing dihydroxy compounds, the bottom product in the column in stage b) of the process remains liquid and conveyable and can therefore be transferred, in a manner which is simple in terms of process engineering, to a further column in which the dihydroxy compound is obtained via the top and a bottom product which is once again liquid or conveyable is obtained at the bottom, which product can likewise be fed in a simple manner to the incineration stage.

In general, a substantial simplification of the treatment of the residues containing dihydroxy compounds is therefore achieved, resulting in considerable savings.

The novel process is illustrated below, once again using the preparation of polybutylene terephthalate as an example; however, it is once again emphasized that it is also suitable for the preparation of other polyesters known to a person skilled in the art.

First, dimethyl terephthalate and 1,4-butanediol (the latter in an excess of 5–60, preferably 10–45, mol are reacted with one another at from 150° to 220° C. at from 0.7 to 1.5 bar for from 30 to 90, preferably from 40 to 70, minutes, transesterification taking place and the methanol formed, together with excess butanediol and small amounts of oligomeric and polymeric compounds and residual amounts of dimethyl terephthalate, being transferred with the vapors to a column into which a liquid residue containing dihydroxy compounds, as obtained, for example, in the distillation of 1,4-butanediol or 1,6-hexanediol, is simultaneously introduced. The composition of the residue is not subject per se to any particular restriction, provided that it is in liquid form and no compounds which interfere with the separation in the column are present. This is generally the case for the residues described, which are obtained from the distillation of butanediol and hexanediol.

The addition is preferably effected in the middle or in the lower part of the column, and the amount added is in general from 0.05 to 5, preferably from 0.1 to 0.3, kg per kg of vapors transferred to the column.

In the column in stage b) of the novel process, the low-boiling methanol is separated off via the top and the added residue containing dihydroxy compounds is discharged with the usual bottom product from the column. Since the product to be discharged is in liquid form or at least conveyable owing to the addition of the residue described, the discharge can be carried out in a simple manner in terms of process engineering and in particular continuously, which was not possible in the case of a waxy or pasty or solid consistency of the bottom products, as obtained by the conventional processes.

This considerable simplification of the handling of this residue results in markedly lower costs.

A further decisive advantage of the novel process is that the bottom product obtained in the working up in the column in stage b), with the aim of recovering butanediol, likewise remains liquid and conveyable and can thus in turn be fed, in a manner which is simple in terms of process engineering, to the incineration stage. This once again results in a simplification and cost savings compared with the conventional processes.

Thus, the addition of a residue containing dihydroxy compounds in stage b) of a transesterification/polycondensation process results in considerable cost benefits without, for example, significantly increasing the amount of the substances which are finally to be incinerated. Since the residues added according to the invention would in any case be added in the incineration stage, which in the end is also advantageous according to the novel process, there are no additional costs which might reduce the cost benefit.

In principle, the added residue is used only in the column in stage b) and in the downstream working-up column as a transport medium for the bottom products which otherwise can no longer be conveyed, and said residue does not itself intervene in the separation processes or reactions.

EXAMPLE

In a stirred kettle, 992 kg/h of dimethyl terephthalate, 640 kg/h of 1,4-butanediol and 1 kg/h of tetrabutyl orthotitanate as a catalyst were reacted at 195° C. and 1 bar in an average residence time of 45 minutes. The vapors liberated in the reaction were transferred continuously to a column, in the middle of which 80 kg/h of a liquid residue obtained in the distillation of 1,4-butanediol (containing 1,4-butanediol, 2-methyl-1,5-pentanediol, 1,6-hexanediol, 2-methyl-1,6-hexanediol and 1,2,5-pentanetriol as main components) were added.

Methanol was continuously discharged at the top of this column, and a liquid bottom product at the bottom of the column. The bottom product was separated in a further column into butanediol and a conveyable bottom product, and the latter was fed via a pipeline to an incineration means.

The column for separating off the methanol could be operated without problems, and the residue could be discharged via a pipeline without problems; without the addition of the residue as in the novel process, the bottom product had a waxy to pasty consistency and could not be readily discharged via pipelines.

We claim:

1. In a process for working up residues which contain dihydroxy compounds and are obtained in the preparation of polyesters by reacting dicarboxylic acids or their esters or ester-forming derivatives with dihydroxy compounds, a) in a first stage a diester of a dicarboxylic acid with an alkanol is subjected to transesterification with a molar excess of a dihydroxy compound, b) the vapors which are obtained in stage 1) and which contain predominantly the alkanol formed in the transesterification plus excess dihydroxy compounds and oligomeric and polymeric reaction products are transferred to a column in which the alkanol is separated off via the top and the other products are separated off as a bottom product, and the dihydroxy compound is then separated from the bottom product, the improvement which comprises adding a liquid residue containing dihydroxy compounds from a separate distillation procedure to stage b) of the process, and discharging the bottom product in substantially liquid form from the column and then subjecting the bottom product to a further distillation treatment for recovering the dihydroxy compound and yielding a conveyable final bottom product.

2. The improved process of claim 1, wherein dimethylterephthalate is subjected to transesterification in stage a) with a molar excess of 10 to 45% of 1,4-butanediol.

* * * * *